United States Patent [19]

Meakin

[11] 4,225,600
[45] Sep. 30, 1980

[54] COMPOSITIONS AND METHODS FOR TREATING CERTAIN SKIN CONDITIONS

[75] Inventor: Brian C. Meakin, East Leake, England

[73] Assignee: Fisons Limited, London, England

[21] Appl. No.: 897,415

[22] Filed: Apr. 18, 1978

[30] Foreign Application Priority Data

May 4, 1977 [GB] United Kingdom ............... 18617/77

[51] Int. Cl.² ..................... A61K 31/47; A61K 31/41; A61K 31/35
[52] U.S. Cl. .................................. 424/258; 424/269; 424/283
[58] Field of Search ....................... 424/283, 269, 258

[56] References Cited

U.S. PATENT DOCUMENTS

3,484,445   12/1969   Lee et al. .............................. 260/294

OTHER PUBLICATIONS

Chemical Abstracts, 65:3887g, (1966).
Chemical Abstracts, 64:17546a, (1966).

*Primary Examiner*—Leonard Schenkman
*Attorney, Agent, or Firm*—Merriam, Marshall & Bicknell

[57] ABSTRACT

There is described a pharmaceutical composition suitable for application to the skin and comprising, as active ingredient, a compound of formula I,

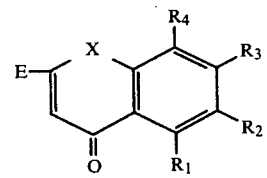

in which $R_1$ represents hydrogen, hydroxy or $-NR_5R_6$, in which $R_5$ and $R_6$, which may be the same or different each represents hydrogen or alkyl C 1 to 6, an adjacent pair of $R_2$, $R_3$ and $R_4$ form a $-(CH_2)_4-$ chain and the remaining substituent $R_2$ or $R_4$ represents alkyl C 1 to 9, E represents a 5-(1H)tetrazolyl- or a $-COOH$ group, and X represents oxygen or a group $-NR_7-$ in which $R_7$ may be hydrogen or alkyl C 1 to 6, or a pharmaceutically acceptable derivative thereof, together with a mixture of a solvent for the active ingredient and a non-solvent for the active ingredient, the solvent and the non-solvent being miscible in the relevant proportions and the proportion of the non-solvent being such that the active ingredient forms a solution in the mixture.

14 Claims, No Drawings

COMPOSITIONS AND METHODS FOR TREATING CERTAIN SKIN CONDITIONS

This invention relates to a novel pharmaceutical composition.

According to the invention there is provided a pharmaceutical composition suitable for application to the skin and comprising, as active ingredient, a compound of formula I,

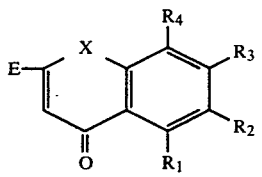

in which $R_1$ represents hydrogen, hydroxy or —$NR_5R_6$, in which $R_5$ and $R_6$, which may be the same or different each represents hydrogen or alkyl C 1 to 6, an adjacent pair of $R_2$, $R_3$ and $R_4$ form a —$(CH_2)_4$— chain and the remaining substituent $R_2$ or $R_4$ represents alkyl C 1 to 9, E represents a 5-(1H)tetrazolyl- or a —COOH group, and X represents oxygen or a group —$NR_7$—in which $R_7$ may be hydrogen or alkyl C 1 to 6, or a pharmaceutically acceptable derivative thereof, together with a mixture of a solvent for the active ingredient and a non-solvent for the active ingredient, the solvent and the non-solvent being miscible in the relevant proportions and the proportion of the non-solvent being such that the active ingredient forms a solution in the mixture.

The solution is desirably saturated or near saturated with active ingredient.

The solvent may, for example, be a suitable organic solvent such as propylene glycol, and the non-solvent may be, for example, water. The mixture is desirably formulated as a gel, e.g. by the incorporation of a suitable thickening agent. Suitable thickening agents include bentonite, soluble cellulose derivatives (e.g. sodium carboxy methyl cellulose, hydroxypropyl methyl cellulose), aluminum magnesium silicate, polyvinyl alcohol, and in particular 'Carbopol 934' which is a polymer of acrylic acid cross linked with allylsucrose. To produce a gel at least some of the carboxyl groups of the 'Carbopol' should be neutralised and we prefer to use an organic base, e.g. triethylamine or diisopropanolamine, which forms a salt with the 'Carbopol' which is compatible with the solvent system. It is desirable to control the pH of the mixture to ensure that as much as possible of the active ingredient is in the form (e.g. acid or salt) which is most readily absorbed by the skin. When a gel is used the pH should be adjusted to ensure that the gel has the desired viscosity. We prefer the compositions of the invention to have a pH in the range 4 to 6, and preferably about 5.

Other ingredients, e.g. humectants, antioxidants, perfumes and pigments may also be present if desired.

Pharmaceutically acceptable derivatives of the compounds of formula I include pharmaceutically acceptable salts, and, when E is a —COOH group, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g piperidine or morpholine. Suitable esters include simple lower alkyl (C 1 to 6) esters, e.g. the ethyl ester, esters derived from alcohols containing basic groups, e.g. di-lower alkyl amino substituted alkanols such as the β-(diethylamino)-ethyl ester, and acyloxy alkyl esters, e.g. a lower acyloxy-lower alkyl ester such as the pivaloyloxymethyl ester, or a bis-ester derived from a di-hydroxy compound, e.g. di(hydroxy-lower alkyl) ether, e.g. the bis-2-oxapropan-1,3-diyl ester. The pharmaceutically acceptable acid addition salts of the basic esters and of those compounds in which $R_1$ is a group —$NR_5R_6$, e.g. the hydrochloride, the hydrobromide, the oxalate, the maleate or the fumarate may also be used. The esters may be made by conventional techniques, e.g. esterification, transesterification or reaction of the acid, or a salt thereof, with an appropriate compound containing a good leaving group. The amides may be, for example, unsubstituted or mono- or di- C 1 to 6 alkyl amides and may be made by conventional techniques, e.g. reaction of an ester of the corresponding acid with ammonia or an appropriate amine. We prefer to use a free acid of formula I or a sodium salt thereof.

We prefer $R_5$ and $R_6$ to be selected from hydrogen and alkyl C 1 to 3, e.g. methyl or ethyl. We also prefer $R_1$ not to be hydrogen (e.g. to be —OH), $R_2$ and $R_3$ to together form the —$(CH_2)_4$—chain, and $R_4$ to be alkyl C 2 to 4, e.g. propyl. $R_7$ is preferably C 1 to 4, e.g. ethyl, however we prefer X to be oxygen. We also prefer E to be a —COOH group.

Specific compounds of formula I which may be mentioned are:

5-Amino-6,7,8,9-tetrahydro-4-oxo-10-propyl-4H-naphtho[2,3-b]pyran-2-carboxylic acid, 6,7,8,9-Tetrahydro-5-hydroxy-4-oxo-10-propyl-4H-naphtho[2,3-b]pyran-2-carboxylic acid, 5-Dimethylamino-6,7,8,9-tetrahydro-4-oxo-10-propyl-4H-naphtho[2,3-b]pyran-2-carboxylic acid, 7,8,9,10-Tetrahydro-5-hydroxy-4-oxo-6-propyl-4H-naphtho[1,2-b]pyran-2-carboxylic acid, 1-Ethyl-5-hydroxy-6-propyl-7,8,9,10-tetrahydro-4(1H)-benzo[h]quinolinone-2-carboxylic acid, 5-(6,7,8,9-Tetrahydro-5-hydroxy-4-oxo-10-propyl-4H-naphtho[2,3-b]pyran-2-yl)tetrazole, and 6,7,8,9-Tetrahydro-4-oxo-10-propyl-4H-naphtho[2,3-b]pyran-2-carboxylic acid.

The active ingredient may be applied topically to the skin tissues of the mammal, notably man, cat, dog or horse.

The active ingredient may be present in the compositions of this invention in an amount of from 0.01 to 10%, preferably 0.1 to 5% and more preferably 0.3 to 5% by weight of the total composition.

The compositions according to the invention may be made by adding a solution of active ingredient in a mixture of base and solvent to a dispersion of 'Carbopol' in the non-solvent. To avoid precipitation of active ingredient during the preparation of a gelled mixed solvent product a solution of active ingredient in the solvent may be added to the non-solvent. The final pH of the formulation may be controlled by the addition of an appropriate quantity of acid or base.

The composition is preferably administered to the skin of a patient merely by smearing or spreading over the area of the skin affected or likely to be affected.

The rate of application of the composition will depend upon the severity and the surface area of the disorder to be treated and repeated applications may be made at intervals during the day, e.g. from 1 to 6 times, and preferably twice, a day. The composition may be applied prophylactically, but is more usually applied to an area which is already affected.

The compositions of the invention find use in the treatment of various disorders in mammals, notably man, cats, dogs and horses.

According to the invention therefore we also provide a method for the treatment or prevention of a condition, in a mammal, e.g. man, cats, dogs and horses, which conditions involves skin mast cells and/or delayed (cellular) hypersensitivity reactions, which method comprises administering an effective amount of a composition according to the invention to a mammal having, or susceptible to, such a condition.

Specific conditions in man and other animals which may be treated by the application of the composition of the invention include contact dermatitis to a specific allergen, e.g. nickel, chromates, synthetic resins, applied medicaments and other chemicals (Rook A., Wilkinson DS and Ebling FJS 1972 Textbook of Dermatology 2nd Edition Blackwell, Oxford Chapters 14 and 15).

Dermatoses which may be treated include contact sensitivity, e.g. to chromium, nickel or an antibiotic, eczemas, drug eruptions, psoriasis, dermatitis herpetiformis, atopic dermatitis, apthous ulcers, Behcet's syndrome, pemphigus, urticaria, urticaria pigmentosa, the ulcers of Crohn's disease, pyoderma gangrenosum and chronic skin ulcers, notably those affecting man in tropical climates. The composition is of particular use in the treatment of atopic eczema in man. When pemphigus, apthous ulcers of Behcet's syndrome are to be treated the composition may be applied to the mucous membrane. However we prefer not to apply the composition to the mucous membranes.

The amount of the composition to be administered will of course vary with the condition to be treated, the animal or patient to be treated, the particular derivative used and the mode of administration. For man the indicated daily dosage is in the range of from 1 mg to 3500 mg preferably 1 mg to 3000 mg and more preferably from 1 mg to 600 mg, of active ingredient which may be administered in divided doses from 1 to 6 times a day. When administering the active ingredient topically the dosage is difficult to control, but will depend in general on the size and condition of the area to be treated.

The invention is illustrated, but in no way limited by the following Example.

The invention is illustrated, but in no way limited by the following Example.

EXAMPLE

| Gel | |
|---|---|
| Compound of formula I | 0.1% w/w |
| 'Carbopol' 934 | 1.5% w/w |
| Triethylamine | 0.46% w/w |
| Propylene glycol | 31.34% w/w |
| Distilled water | 66.6% w/w |

The compound of formula I is typically present in the above formulation in from 0.01 to 10% notably 0.1 to 3%, by weight.

I claim:

1. A pharmaceutical gel composition suitable for application to the skin and comprising as active ingredient, about 0.01 to 10% by weight of a compound of formula I,

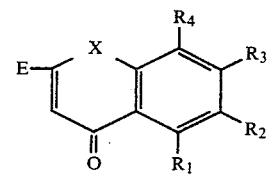

in which $R_1$ represents hydrogen, hydroxy or $-NR_5R_6$, in which $R_5$ and $R_6$, which may be the same or different each represents hydrogen or alkyl C 1 to 6, an adjacent pair of $R_2$, $R_3$ and $R_4$ form a $-(CH_2)_4-$ chain and the remaining substituent $R_2$ or $R_4$ represents alkyl C 1 to 9, E represents a 5-(1H)tetrazolyl- or a $-COOH$ group, and X represents oxygen or a group $-NR_7-$ in which $R_7$ may be hydrogen or alkyl C 1 to 6, or a pharmaceutically acceptable salt, or, when E is a $-COOH$ group a lower alkyl ester thereof, an ester thereof derived from a di-lower alkyl amino substituted alkanol, a lower acyloxy-lower alkyl ester thereof or a bis-ester thereof derived from a di(hydroxy-lower alkyl)ether, or an unsubstituted or a mono- or di-C 1 to 6 alkyl amide thereof, together with a mixture of a solvent for the active ingredient and a non-solvent for the active ingredient, the solvent and the non-solvent being miscible in the relevant proportions and the proportion of the non-solvent being such that the active ingredient forms a substantially saturated solution in the mixture.

2. A composition according to claim 1, wherein the solvent is propylene glycol and the non-solvent is water.

3. A composition according to claim 1, wherein the gel includes bentonite, sodium carboxy methyl cellulose, hydroxypropyl methyl cellulose, aluminum magnesium silicate, or a polyvinyl alcohol.

4. A composition according to claim 1, wherein the gel includes a polymer of acrylic acid cross linked with allylsucrose.

5. A composition according to claim 4, wherein the polymer is neutralised with an organic base to form a salt which is compatible with the solvent system.

6. A composition according to claim 1, wherein the pH of the composition is such that the active ingredient is in the form which is most readily absorbed by the skin.

7. A composition according to claim 1, wherein the composition has a pH in the range 4 to 6.

8. A composition according to claim 7, wherein the composition has a pH of 5.

9. A composition according to claim 1, wherein the active ingredient comprises from 0.1 to 5% by weight of the composition.